United States Patent
Zhang et al.

(10) Patent No.: US 11,371,905 B2
(45) Date of Patent: Jun. 28, 2022

(54) METHODS FOR DETECTING LEAKAGE IN PERMEABILITY MEASUREMENT SYSTEM

(71) Applicant: Saudi Arabian Oil Company, Dhahran (SA)

(72) Inventors: Jilin Jay Zhang, Cypress, TX (US); Hui-Hai Liu, Katy, TX (US); Huangye Chen, Cypress, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 186 days.

(21) Appl. No.: 16/857,294

(22) Filed: Apr. 24, 2020

(65) Prior Publication Data

US 2020/0370989 A1    Nov. 26, 2020

Related U.S. Application Data

(60) Provisional application No. 62/852,509, filed on May 24, 2019.

(51) Int. Cl.
 *G01M 3/00* (2006.01)
 *G01M 3/26* (2006.01)
 *G01N 15/08* (2006.01)

(52) U.S. Cl.
 CPC ............ *G01M 3/26* (2013.01); *G01N 15/082* (2013.01); *G01N 15/0806* (2013.01)

(58) Field of Classification Search
 CPC ... G01N 15/08; G01N 15/0806; G01N 15/082
 See application file for complete search history.

(56) References Cited

U.S. PATENT DOCUMENTS 3,729,983 A * 5/1973 Coppens ............... G01M 3/229
                                                   73/40.7
4,984,450 A   1/1991 Burger
                (Continued)

FOREIGN PATENT DOCUMENTS

CN    107655805 A    2/2018
CN    107831103 B    3/2018
         (Continued)

OTHER PUBLICATIONS

International Search Report and Written Opinion for International Application No. PCT/US2020/034149 report dated Jul. 31, 2020; pp. 1-16.

*Primary Examiner* — Nguyen Q. Ha
(74) *Attorney, Agent, or Firm* — Bracewell LLP; Constance G. Rhebergen; Linda L. Morgan

(57) ABSTRACT

Methods and systems for detecting leakage in a permeability measurement system. The method includes connecting a plurality of flow lines to a first dimension of a core sample assembly, connecting one or more flow lines to a second dimension of the core sample assembly, placing the core sample assembly with the connections in a measurement cell such that the flow lines are accessible from outside of the measurement cell, connecting one or more gas sensors to one end of each of the flow lines, connecting an inlet of the measurement cell to a gas tank, setting fluid pressure inside the measurement cell to a predetermined value, and detecting a leakage in the core sample assembly by the one or more gas sensors coupled to the flow lines.

20 Claims, 12 Drawing Sheets

(56) References Cited

U.S. PATENT DOCUMENTS

| | | | |
|---|---|---|---|
| 6,050,133 A | 4/2000 | Achter et al. | |
| 7,980,117 B2 | 7/2011 | Wetzig et al. | |
| 8,261,594 B2 | 9/2012 | Maehira et al. | |
| 9,038,441 B2 | 5/2015 | Downing | |
| 10,502,673 B2 | 12/2019 | Chertov et al. | |
| 2007/0157704 A1* | 7/2007 | Jenneus | G01M 3/226 73/40.7 |
| 2017/0167964 A1 | 6/2017 | Liu et al. | |
| 2018/0364142 A1* | 12/2018 | Georgi | G01N 33/241 |
| 2019/0346336 A1 | 11/2019 | Regef | |

FOREIGN PATENT DOCUMENTS

| | | | |
|---|---|---|---|
| CN | 110296921 A | 10/2019 | |
| JP | 2009162680 A | 7/2009 | |
| WO | WO-2020242915 A1 * | 12/2020 | G01M 3/229 |

* cited by examiner

METHODS FOR DETECTING LEAKAGE IN PERMEABILITY MEASUREMENT SYSTEM

CROSS-REFERENCE TO RELATED APPLICATIONS

This application claims priority of U.S. Provisional Application No. 62/852,509, titled "METHODS FOR DETECTING LEAKAGE IN A PERMEABILITY MEASUREMENT SYSTEM," which was filed on May 24, 2019, the entire contents of which are incorporated herein by reference.

TECHNICAL FIELD

This disclosure generally relates to methods and systems for determining permeability and porosity of a subsurface rock formation. More specifically relates to methods for detecting leakage in a system for determining permeability and porosity of a subsurface rock formation.

BACKGROUND

Unlike conventional reservoirs, pores in shale formations are typically in the nanometer scale. In these nano pores, a non-negligible portion of gas molecules collides more often with the pore wall than with other molecules, and thus so-called "slip flow" and Knudsen diffusion occur. Previous studies on gas flow in shale matrix found that the gas permeability in shale is a function of the pore gas pressure because the slip flow and Knudsen diffusion effect becomes significant when the pore gas pressure is a few hundred pounds per square inch (psi) or less.

Shale gas permeability as a function of pore gas pressure, resulting from "slip flow" and diffusion processes, is critical for characterizing and modeling gas flow in a shale gas reservoir. However, this important pore gas pressure-dependency is usually ignored because of the lack of a practical and efficient technique that can be used routinely for determining the pressure-dependent shale gas permeability.

Pressure dependence has an impact on predicted gas-production rate. There are currently two approaches to measure the pressure dependence of gas permeability in the laboratory. The first one is to simply perform a number of pulse-decay permeability tests under different gas pressures. The results of these tests provide gas permeability values for a number of gas pressures. Initially, the system is in equilibrium with a given gas pressure. A small pressure pulse, typically 5-10% of the pore pressure, is then introduced into the upstream gas reservoir, such that the pulse does not have a significant disturbance to the gas pressure in the system. The pressures at the two gas reservoirs are monitored as a function of time. The pressure evolution results are fitted using analytical solutions, with permeability being a fitting parameter. However, it generally takes a relatively long time to equilibrate the test system from one test pressure to the next one.

The other approach to determine the pressure dependence is to first develop a formulation of gas permeability as a function of gas pressure and then to estimate values for parameters in the formulation by numerically matching the relevant test results under different gas pressure conditions. Test results using this method are generally different from pulse-decay tests because the pressure pulse is not limited to a small value, for example 5-10% of the pore pressure. The numerical model is flexible enough to incorporate the pulse disturbance to the system. However, non-uniqueness of parameter estimation could be a problem for inverse modeling. Also, the accuracy of estimated results from this approach is ultimately determined by the formulation used for gas permeability as a function of gas pressure, which is not fully established yet.

For unconventional shale reservoirs, one of the challenges is to determine the matrix permeability, which is a key parameter for characterizing unconventional reservoirs and for modeling flow processes. Measuring the permeability of extremely small magnitude, for example, a few nano Darcies to a couple of hundred nano Darcies, in a lab is not a trivial task for three reasons. First, the gas permeability is sensitive to the effective stress. Second, the gas permeability is also a function of pore pressure for a given effective stress due to diffusion effects in small pores with a diameter of a few nanometers. Third, the use of multiple pressure transducers and mechanical pumps in the lab permeability measurement system further complicates the design and implementation of the lab equipment. Currently, a pulsed decay method is often used to measure the permeability for unconventional rock samples. It involves measuring a first permeability at a first pore pressure and effective stress, and then equilibrating the system at a second pore pressure and effective stress before measuring a second permeability. However, the measured permeability or porosity of the subsurface formation is extremely sensitive to any leakage in the system.

SUMMARY

Accordingly, there is a need for an improved system for detecting leakage in a system for determining permeability and porosity of a subsurface rock formation.

There are many fluid/gas leakage test systems that are currently being used to perform these measurements. For example, some use helium outside the test system and then detect the helium resulting from the leakage from the inside of the test system. However, these methods mix air and helium outside the test system so that helium is the minor component of the gas mixture. In such testing, at least a partial vacuum is pulled on the system such that if there are any leaks helium will be detected as it leaks into the interior of the system. In such testing, the problem is that this detection method is limited to determining whether the system has a leak, not precisely where it is leaking.

The systems and methods according to the some embodiments put the test system (a sample assembly) inside a measurement cell in which pressurized helium is used as helium detection is more sensitive. Additionally, creating a vacuum inside of the test system is no longer needed. Secondly, the some embodiments allows for detecting the precise location of any leaks.

Accordingly, one embodiment is a method for detecting leakage in a permeability measurement system. The method includes extracting a core sample from a subsurface formation, inserting the core sample in a cylindrical sleeve to form a sample assembly, connecting a plurality of flow lines along the length of the core sample, connecting a first flow line to the first end of the core sample, connecting a second flow line to the second end of the core sample, and connecting a gas sensor to ends of each of the flow lines. In one embodiment, the inner diameter of the sleeve is approximately equal to the diameter of the core sample.

The method further includes placing the sample assembly with the connections in a measurement cell such that the flow lines are accessible from outside of the measurement cell, connecting an outlet of the measurement cell to a gas tank, setting fluid pressure inside the measurement cell to a predetermined value and detecting a leakage in the system by one or more of the gas sensors connected to one end of each of the flow lines. The core sample may have a cylindrical shape with a length, a diameter, a first end, and a second end.

The method may further include saturating the core sample with a predetermined gas at a predetermined pressure prior to placing the sample assembly inside the measurement cell. The gas sensor may include a helium gas sniffer, and may include any type of sensor including but not limited to a combustible gas sensor, a photoionization detector, an infrared point sensor, an infrared imaging sensor, an ultrasonic sensor, an electrochemical gas sensor, a holographic sensor, and a metal-oxide-semiconductor sensor. According to one embodiment, the gas sensor is able to detect a minimum gas flow rate of $1\times10^{-7}$ cubic centimeter per second (cc/s), because the measurement of permeability and porosity of the rock formation can be impacted due to even the slightest leakage in the system, and the method disclosed determines a precise location of the leakage based on the flow line(s) detecting the leakage. The gas tank may include at least one of helium, nitrogen, argon, oxygen, and combinations thereof. Although the above example refer to a shale sample, the core sample may include any of shale, sandstone, or limestone.

Another embodiment is an apparatus for detecting leakage in a permeability measurement system. The apparatus includes a sample assembly comprising a cylindrical sleeve and a core sample of a subsurface formation disposed within the sleeve, the core sample having a cylindrical shape with a length, a diameter, a first end, and a second end. The apparatus further includes a plurality of flow lines connected along the length of the core sample, a first flow line connected to the first end of the core sample, a second flow line connected to the second end of the core sample, and a gas sensor connected to ends of each of the flow lines. The apparatus further includes a measurement cell configured to receive the sample assembly such that the flow lines are accessible from outside of the measurement cell, and a gas tank connected to an outlet of the measurement cell, wherein a fluid pressure inside the measurement cell is set to a predetermined value, wherein the gas sensors are configured to detect a leakage in the system.

BRIEF DESCRIPTION OF THE DRAWINGS

So that the manner in which the features, advantages and objects of the invention, as well as others which may become apparent, are attained and can be understood in more detail, more particular description of the invention briefly summarized above may be had by reference to the embodiment thereof which is illustrated in the appended drawings, which drawings form a part of this specification. It is to be noted, however, that the drawings illustrate only example embodiments of the invention and is therefore not to be considered limiting of its scope as the invention may admit to other equally effective embodiments.

DETAILED DESCRIPTION

The methods and systems of the present disclosure will now be described more fully hereinafter with reference to the accompanying drawings in which embodiments are shown. The methods and systems of the present disclosure may be in many different forms and should not be construed as limited to the illustrated embodiments set forth herein; rather, these embodiments are provided so that this disclosure will be thorough and complete, and will fully convey its scope to those skilled in the art. Like numbers refer to like elements throughout.

Figure 1:
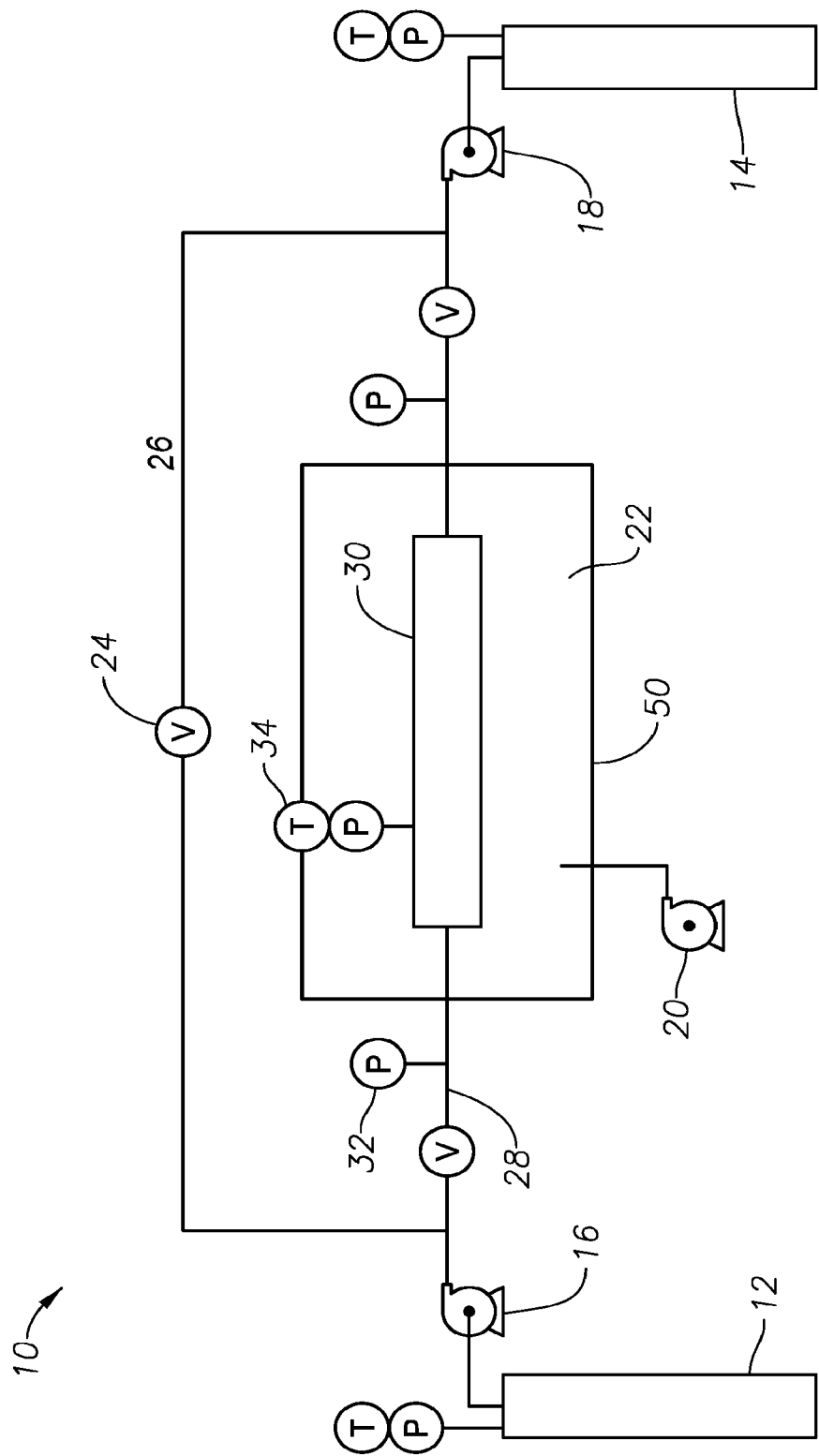
FIG. 1 illustrates an example system for determining permeability and porosity of a subsurface formation, according to one example embodiment of the disclosure.

Turning now to the figures, FIG. 1 illustrates an example system 10 for determining permeability function k(p) and porosity of a subsurface formation, according to some example embodiments of the disclosure. System 10 includes sample 30, such as a shale sample, a limestone sample, or a sandstone sample, in the form of a cylinder or column that may be extracted from the subsurface for determining characteristics of the formation. The sample 30 in a sleeve 52 is placed in a pressure vessel 50 that may contain a confining fluid 22, such as gas, a water-based fluid, or an oil-based fluid. The pressure vessel 50 is coupled to pumps 16, 18 through pressure lines 28, and provides the confining pressure to the sample 30.

System 10 includes an inlet pump 16 configured to pump fluid from a first gas tank 12 into sample 30. The system also includes an outlet pump 18 configured to pump fluid from a second gas tank 14 into sample 30. Both pumps may include one or more pressure and flowrate sensors to measure and control the pressure inside the core sample assembly. Pressure vessel 50 may be equipped with a hydraulic pump 20 that may pump the confining fluid 22 into pressure vessel 50. The pressure vessel 50 may include an apparatus that monitors and regulates the pressure within the pressure vessel 50. Temperature gauges 34 and pressure gauge 32 are coupled to the sample and to the inlet of the core sample, respectively. Both gauges may include high accuracy transducers (with a typical accuracy of 0.01%) to measure temperature and pressure, respectively, in real-time. Inlet 28 to the core sample assembly may be diverted at a plurality of points using bypass valves 24 and an outlet pipe 26 in order to regulate the pore gas pressure (for example, the establishment of the initial pore pressure) in sample 30 which is placed in the pressure vessel 50.

Figure 2A:
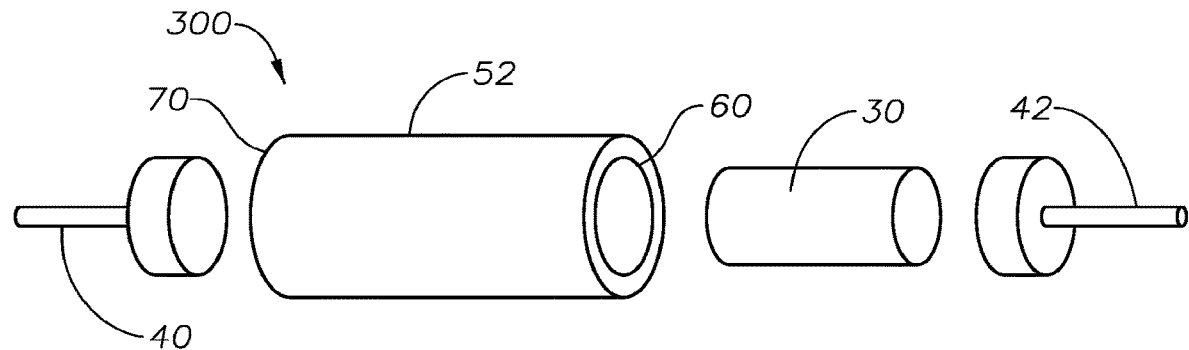
FIGS. 2A-2D illustrate an example apparatus for determining permeability and porosity of a subsurface formation, according to one example embodiment of the disclosure.
Figure 2B:
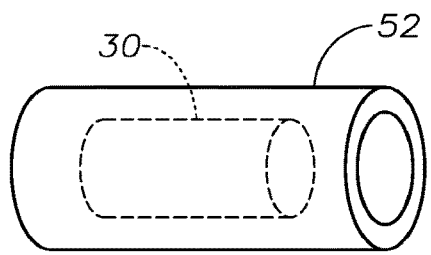
Figure 2C:
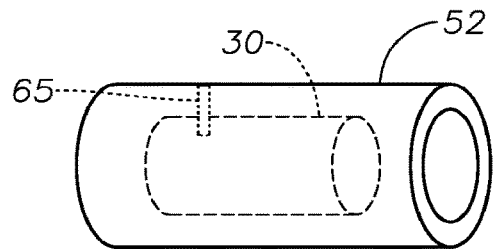

FIGS. 2A-2D illustrate in further detail an example set up for arranging a shale sample assembly 300 in the pressure vessel 50. As illustrated in FIG. 2A, the shale sample 30 is first inserted into a sleeve 52 having a length, a diameter, a first open end 60, and a second open end 70. The shale sample may be enclosed in the sleeve 52 using a first end piece or outlet 42 adapted to be inserted into the first open end 60, and a second end piece or inlet 40 adapted to be inserted into the second open end 70 of the sleeve 52. FIG. 2B illustrates the first step where the shale sample 30 is inserted into a sleeve 52. As illustrated in FIG. 2C, a through hole or a port for pressure measurement 65 is formed through the body of the sleeve 52 and into the body of the sample 30 so as to insert a tubing, such as a tubing 44 (shown in FIG. 2D). A half sleeve 46 may be disposed on the tubular sleeve 52, and the half sleeve 46 may include a second hole corresponding to the first hole 65 on the first sleeve. The tubing 44 may be coupled to a temperature gauge 34 and a pressure gauge 32 as illustrated in FIG. 1, for example. An anchoring device 48 may be used for securing the tubing 44 to the half sleeve 46, thereby forming an assembly. Other fastening devices, such as ring clamps, may be used to secure the half sleeve 46 and the sleeve 52. The inlet 40 and outlet 42 on the sample assembly 300 may be coupled through couplings on the wall or the end caps of the pressure vessel 50 to the pressure lines (such as 28), which may be coupled to the inlet pump 16 and outlet pump 18.

Figure 2D:
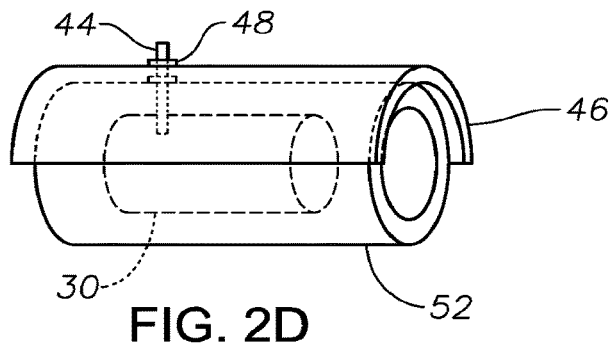
Figure 3:
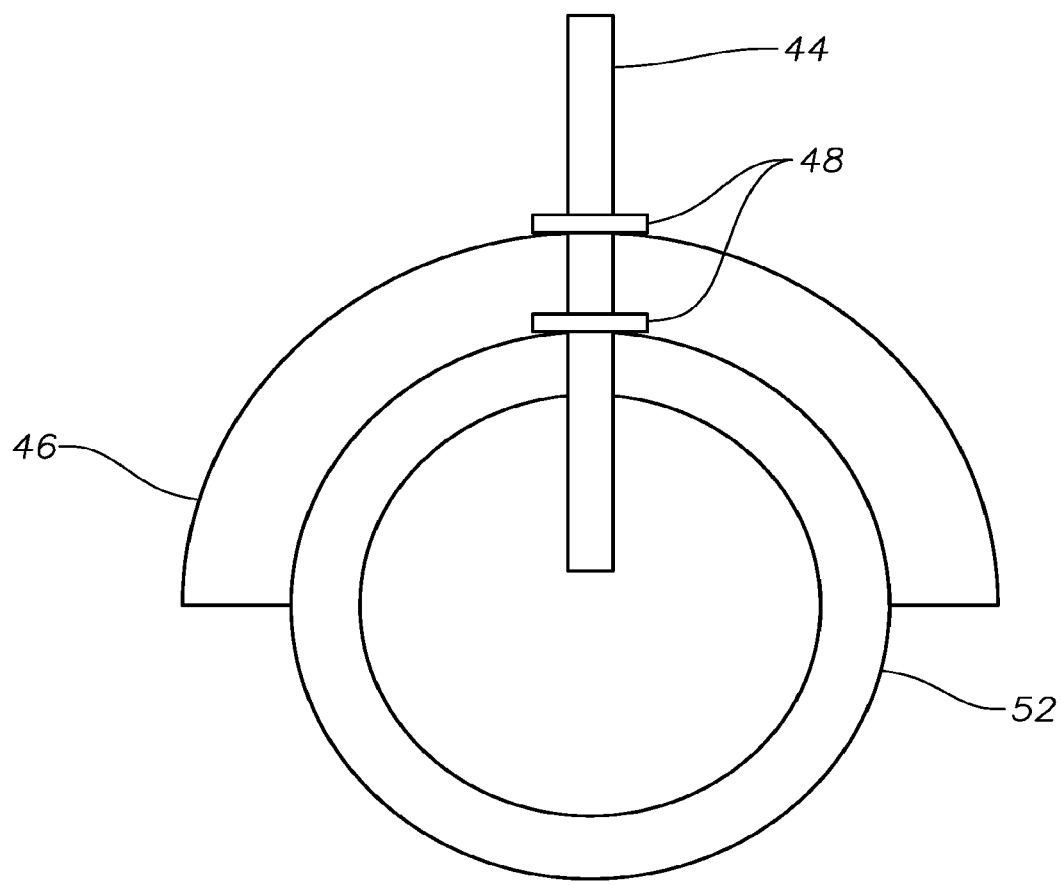
FIG. 3 illustrates a cross-sectional view of an apparatus for determining permeability and porosity of a subsurface formation, according to one example embodiment of the disclosure.

FIG. 3 illustrates a cross-sectional view of the apparatus in FIG. 2D where tubing 44, which in some embodiments may comprise steel, is inserted through the half sleeve 46, sleeve 52, and secured using anchoring devices 48. According to one example embodiment, sleeve 52 and half sleeve 46 may include at least one of rubber and a polymeric material. According to another example embodiment, an inner diameter of the half sleeve 46 may be smaller than the outer diameter of the sleeve 52. According to another example embodiment, a length of the half sleeve 46 is equal to or less than the length of the sleeve 52.

Figure 4A:
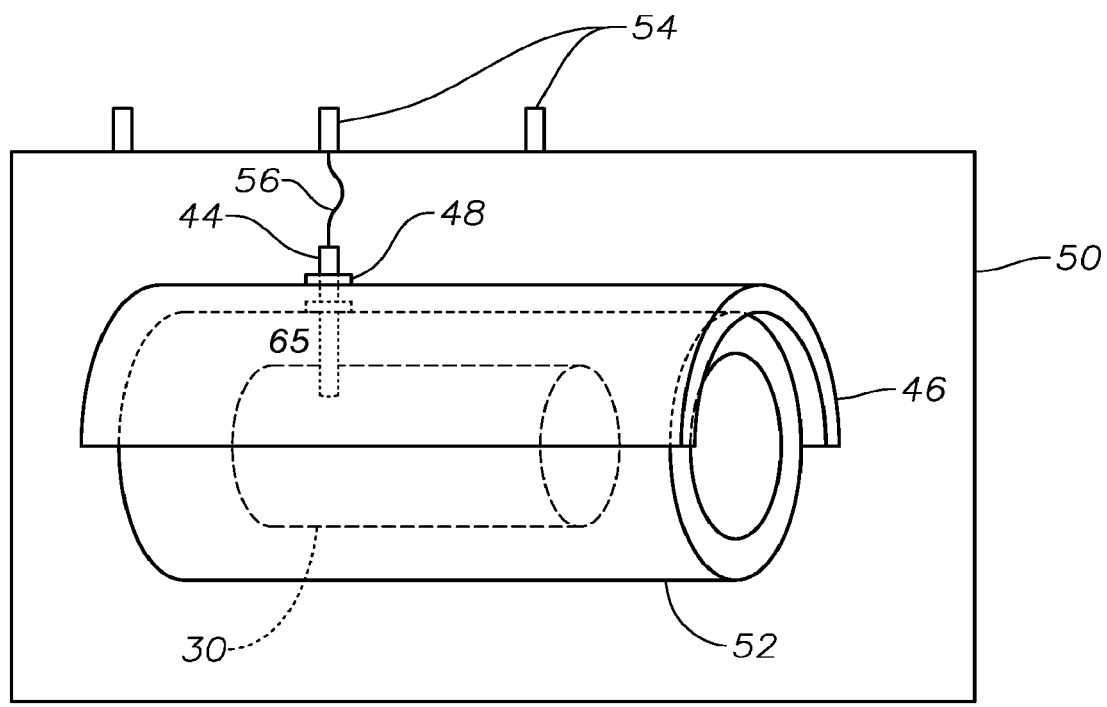
FIGS. 4A and 4B illustrate example apparatuses for determining permeability and porosity of a subsurface formation, according to some example embodiments of the disclosure.
Figure 4B:
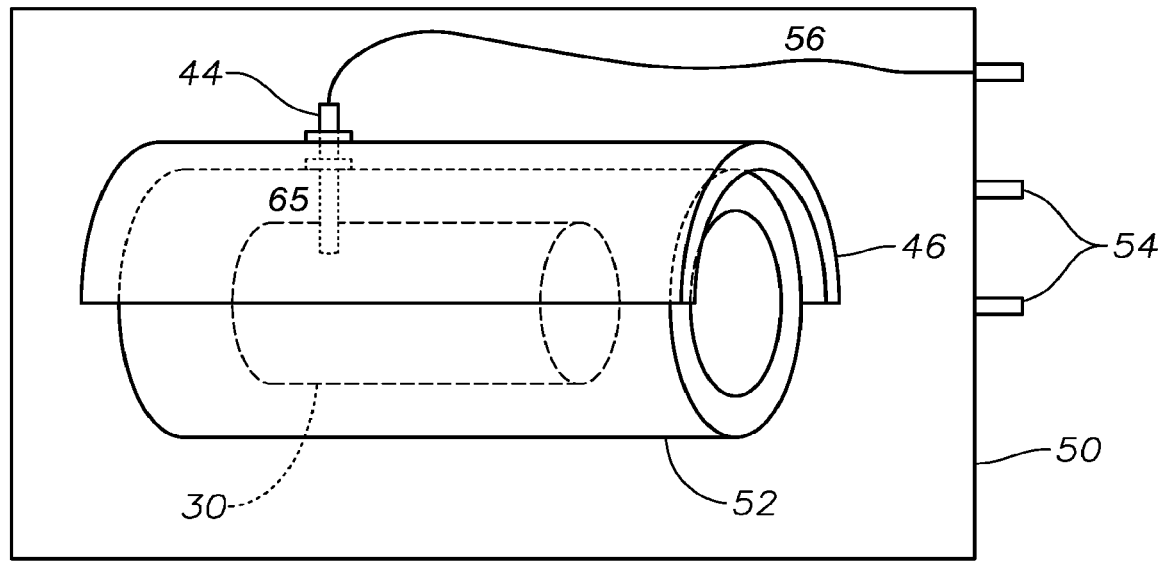

After the sleeve 52 is secured for preventing leakage from the port of pressure measurement 65, the assembly is disposed in the pressure vessel 50, as illustrated in FIG. 4A, for example. The pressure vessel 50 may include a plurality of pressure taps 54, each of which to be coupled a pressure measurement location along the rock sample. FIG. 4B illustrates an alternative arrangement where the pressure taps 54 may be configured along one end of the pressure vessel 50. In this case, multiple measurement locations along the rock sample may be instrumented according to the procedure described in FIGS. 2A-D and 3. According to one example embodiment, one or more temperature gauges 34 and pressure gauges 32 may be coupled to tubing 44 using a flexible line 56.

Analytical Method for Determining Permeability and Porosity of a Subsurface Formation The following sections provide an example method for determining permeability, k, and porosity of a subsurface formation using the system 10 illustrated in FIG. 1. The method is based on an analytical solution to one-dimensional gas flow under certain boundary and initial conditions. The governing mass balance equation for gas flow may be given by Equation 1 as follows:

$$\frac{\partial m}{\partial t} = \frac{\partial}{\partial x}\left(\frac{k\rho}{\mu}\frac{\partial p}{\partial x}\right) \quad (1)$$

where t is time, x is the spatial coordinate (a distance from the inlet of the sample along its axis), k is the permeability, $\mu$, $\rho$, and p are gas viscosity, density and pressure, respectively (note k, $\mu$, $\rho$, are functions of p), and m is the total gas mass per unit volume of the porous medium or apparent gas density, which may be given by Equation 2 as follows:

$$m = \phi\rho + (1-\phi)\rho_a \quad (2)$$

where $\phi$ is porosity and $\rho_a$ is adsorbed gas mass per unit volume of solid phase or the subsurface formation. For conservative gases, the second term on the right hand of Equation 2 can be considered to be zero.

In Equation 1, the storage term can be rewritten as:

$$\frac{\partial m}{\partial t} = \frac{dm}{dp}\frac{\partial p}{\partial t} \quad (3)$$

The present method may relate to isothermal conditions, and therefore m may be considered a function of pressure only. The method may also include relatively high confining stress, for example up to 10,000 psi, such that the effect of mechanical deformation due to pore gas pressure change can be ignored. Accordingly, the contributions of gas density change in pressure to storage can be given by Equation 4 as follows:

$$\frac{dm}{dp} = \phi\frac{d\rho}{dp} + (1-\phi)\frac{d\rho_a}{dp} \quad (4)$$

Taking into consideration an infinite long shale sample in the form of a cylinder/column with gas flow from the inlet (x=0) and subject to the following boundary and initial conditions:

$$p(x,t) = p_i \ (x \geq 0, \ t=0)$$

$$p(x,t) = p_0 \ (x=0, \ t>0) \quad (5)$$

$$p(x,t) = p_i \ (x \to \infty, \ t>0)$$

where $p_i$ is the initial pressure inside the measurement system before the elevated upstream pressure, $p_0$, is applied.

Using the transformation $$\lambda = xt^{-\frac{1}{2}} \quad (6)$$

Equations 5 and 1 can be transformed as follows:

$$p(\lambda) = p_i \quad (\lambda \to \infty) \tag{7}$$

$$p(\lambda) = p_0 \quad (\lambda = 0)$$

and $$-\frac{\lambda}{2}\frac{dm}{dp}\frac{\partial p}{\partial \lambda} = \frac{d}{d\lambda}\left[D(p)\frac{dp}{d\lambda}\right] \tag{8}$$

where $$D(p) = \frac{k\rho}{\mu} \tag{9}$$

Equation 8 is an ordinary differential equation with $\lambda$ as the only independent variable.

Directly integrating Equation 8 for the interval $(\lambda, \infty)$ yields $$D(p) = -\frac{\int_{p_i}^{p} \frac{\lambda}{2}\frac{dm}{dp}dp}{\frac{\partial p}{\partial \lambda}} \tag{10}$$

Equation 10 indicates that D(p) can be fully determined when $p(\lambda)$ is known.

Based on the gas mass balance, the cumulative gas flow into the column (at x=0) can be determined using Equation 11 as follows:

$$M(t) = A\int_0^\infty (m - m_i)dx = A(m - m_i)x\Big|_0^\infty - A\int_{p_0}^{p_i} x\frac{dm}{dp}dp = A\int_{p_i}^{p_0} x\frac{dm}{dp}dp \tag{11}$$

where A is the cross-sectional area of the shale column. Combining Equations 11 and 6 gives $$M(t) = \left(A\int_{p_i}^{p_0}\lambda\frac{dm}{dp}dp\right)t^{\frac{1}{2}} = Bt^{\frac{1}{2}} \tag{12}$$

where B is a slope for the curve of M(t) versus $t^{1/2}$. Combining Equations 4 and 12 gives $$\phi = \frac{B - A\int_{p_i}^{p_0}\lambda\frac{d\rho_a}{dp}dp}{A\int_{p_i}^{p_0}\lambda\frac{d(\rho - \rho_a)}{dp}dp} \tag{13}$$

Equations 10 and 13 may be used for estimating gas permeability and porosity, according to one or more example embodiments of the disclosure.

As illustrated previously, for an infinite long shale column with a uniform initial pore gas pressure, the porosity and permeability can be estimated as a function of pore gas pressure using Equations 10 and 13 from measurement of M(t) and $p(\lambda)$, which are obtained under a constant pressure at the column inlet. It should be noted, however, that the gas compressibility and adsorption parameter, which are functions of pore gas pressure in these equations, may be independently determined or estimated from other tests or existing literature. The adsorption parameter may not be involved if gas used for a test is not reactive.

The test method is consistent with initial and boundary conditions used to obtain Equations 10 and 13. M(t) and $p(\lambda)$ can be effectively and reliably measured from a test run. Initially, shale sample 30 with a confining stress has a uniform gas pore-pressure $p_i$. The confining stress may be significantly higher than the range of pore gas pressure, for example 15-2015 psi, used in the test such that any mechanical deformation due to pore gas pressure variation can be ignored. The sample 30 is long enough, for example 4 inches in length, such that it can be treated as infinitely long for a certain period of test time. The upstream gas reservoir of the shale sample 30 may then be coupled to inlet pump 16 with precise pressure and flowrate controls. The upstream pressure of the core sample 30 may be maintained as a constant $p_0$ by the inlet pump 16. The pressure range between $p_i$ and $p_0$ covers the range of practical interest or the range in which the pressure dependence is important. Cumulative gas mass flow rate into the column inlet, M(t), may be monitored. The pore gas pressure may be measured as a function of time at a given location of shale column. The monitoring locations can be set any location except at the two ends. In one embodiment, measurement can be taken about 1 inch from the column inlet. From the transformation given in Equation 6, $p(\lambda)$ can be obtained from the pressure measurements. The pressure at outlet of the sample 30 is measured to monitor pore gas pressure breakthrough. Pressure breakthrough is considered to occur at the outlet when pressure increases by about 0.1 psi. It should be noted, however, that after pressure breakthrough, the boundary effect from the downstream may be propagated to the measurement point. After time ($t_c$), the length of sample 30 cannot be treated as infinite anymore. Thus, only pressure data before time ($t_c$) can be used to calculate $p(\lambda)$.

The time $t_c$ can be estimated using Equation 14 as follows:

$$t_c = t_b\left[1 + \left(\frac{L_b}{L}\right)^2\right] \tag{14}$$

where $t_b$ is the time of the pressure breakthrough at the outlet of sample 30, L is the length of shale sample 30, and $L_b$ is the distance between a pressure measurement location and column outlet. The previous equation may be obtained by assuming D(p) in Equation 9 to be constant. In this case, the travel distance of the diffusion front resulting from the outlet disturbance may be proportional to the square root of the time since the pressure breaks through at the outlet.

Example System for Detecting Leakage in a Permeability Measurement System

Figure 5A:
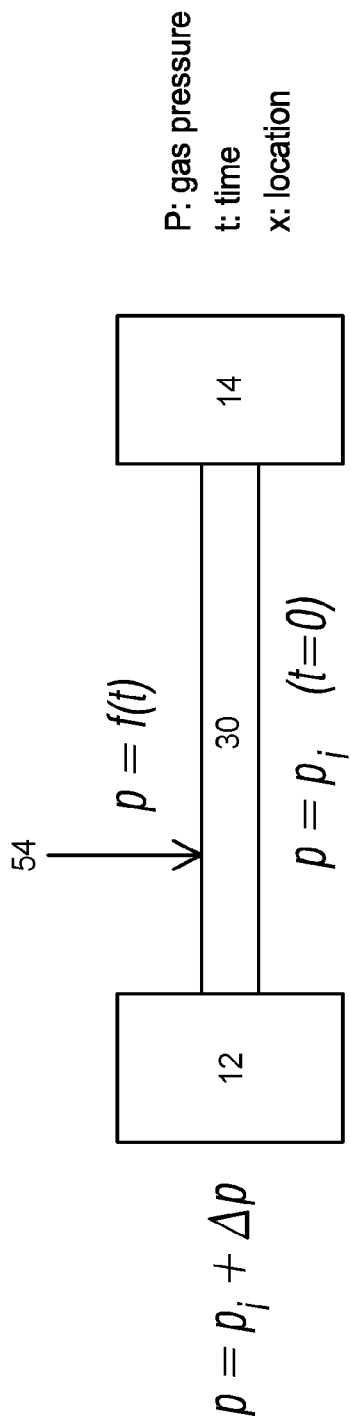
FIGS. 5A and 5B illustrate an example apparatus for detecting leakage in a system for determining permeability and porosity of a subsurface rock formation, according to some example embodiments of the disclosure.
Figure 5B:
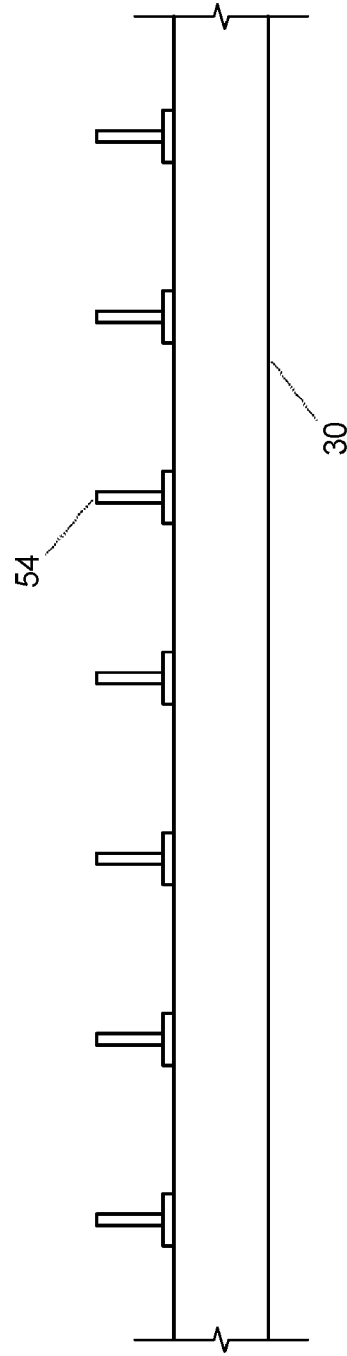

FIGS. 5A and 5B schematically illustrate a method for determining permeability and porosity of a subsurface formation, according to some example embodiments of the disclosure. The method includes at least the following three steps. First, the sample 30 is saturated with a measurement gas, such as nitrogen, at a specified pressure when the sample assembly is inside the cell with confining fluid at a specified confining pressure. Second, a constant pressure in the upstream reservoir 12 is maintained and pressure measurements on multiple side taps 54 along the core sample (as shown in FIG. 5B) are recorded as a function of time during the measurement. Third, the pressure of the downstream reservoir 14 is raised to a value greater than a predetermined pressure threshold.

However, the problem encountered during the measurement is that the confining fluid in the cell (pressure vessel 50) containing core sample assembly 300 sometimes leaks into the core sample 30 through the side holes 65 of the pressure measurement line(s) that connect the core sample 30 to the pressure transducer(s), or the flow line(s) that connect the core sample to the upstream and downstream gas reservoirs. Because of this, valuable time is wasted on cleaning the flow lines or pressure measurement lines before performing the next step.

Figure 6A:
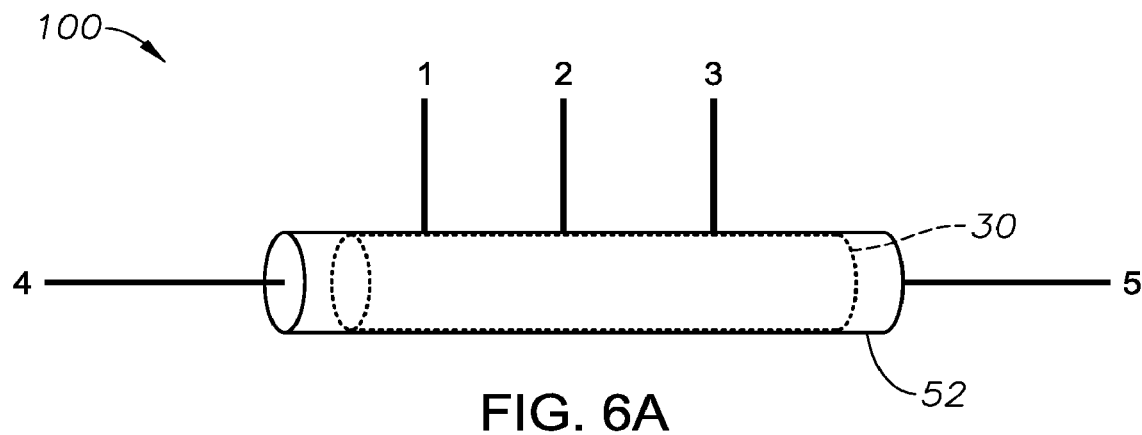
FIGS. 6A-6E illustrate example steps in a method for detecting leakage in a system for determining permeability and porosity of a subsurface rock formation, according to some example embodiments of the disclosure.

FIGS. 6A-6E illustrate an example system 100 for detecting leakage in a permeability measurement system, according to some example embodiments of the disclosure. In FIG. 6A, sample 30 is placed in the sleeve 52 with multiple side lines 1, 2, 3 that can be coupled on the side of the sample 30 through side taps for performing pressure measurement. Flow lines 4, 5 are coupled to the inlet and outlet of the rock sample after the endcaps are properly installed on the sleeve 52. Each of the flow lines 1, 2, 3, 4, 5 may be connected to as gas sensor having a transducer or a gas sniffer, for example.

Figure 6B:
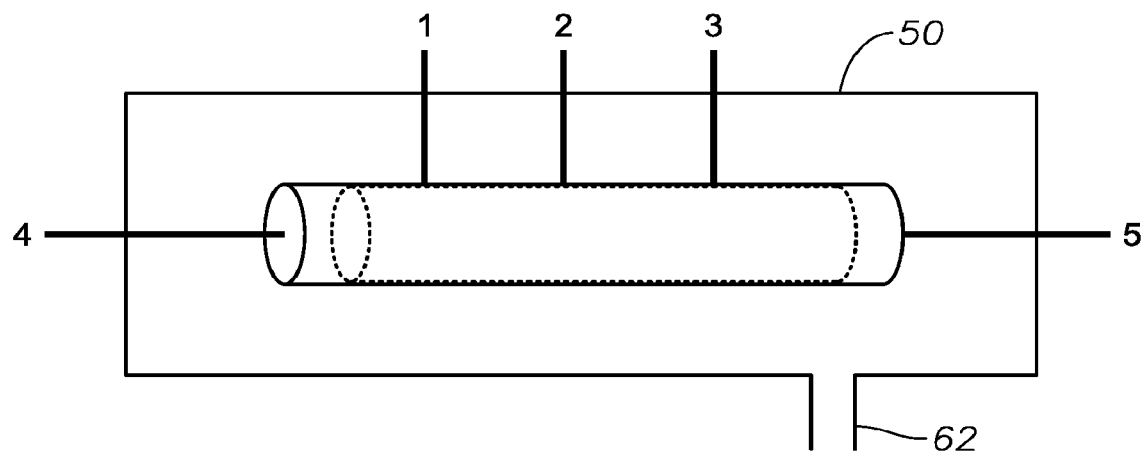
Figure 6C:
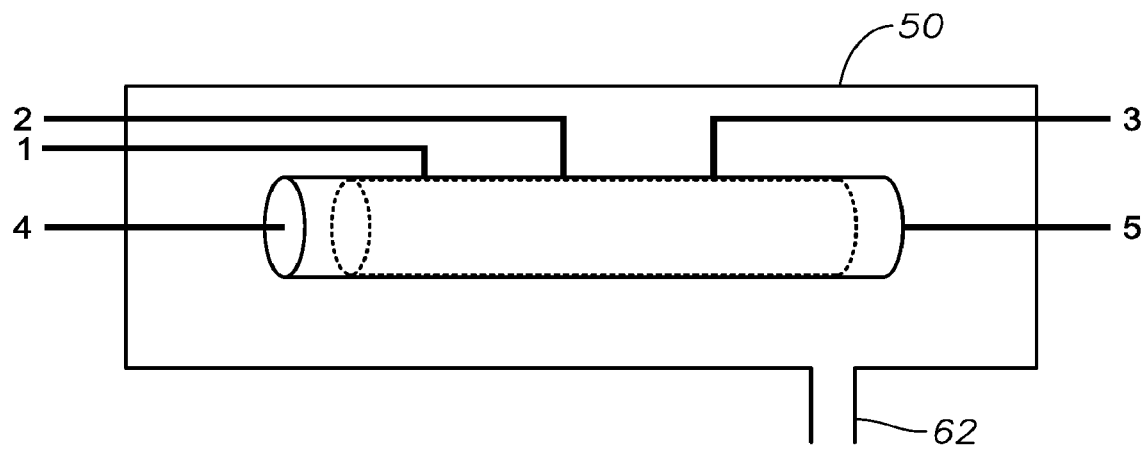
Figure 6D:
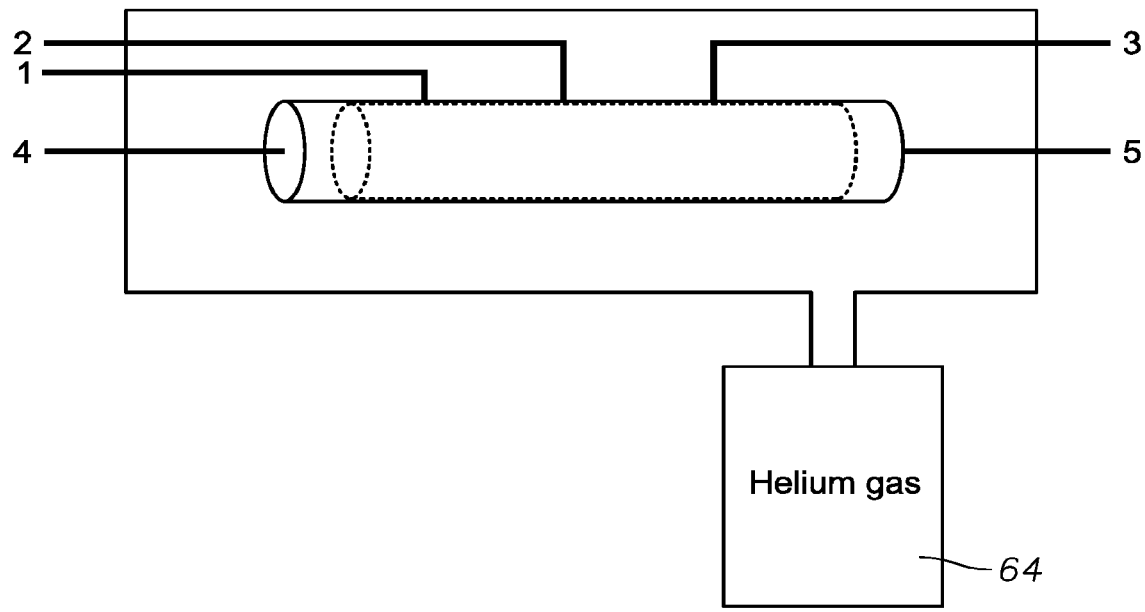
Figure 6E:
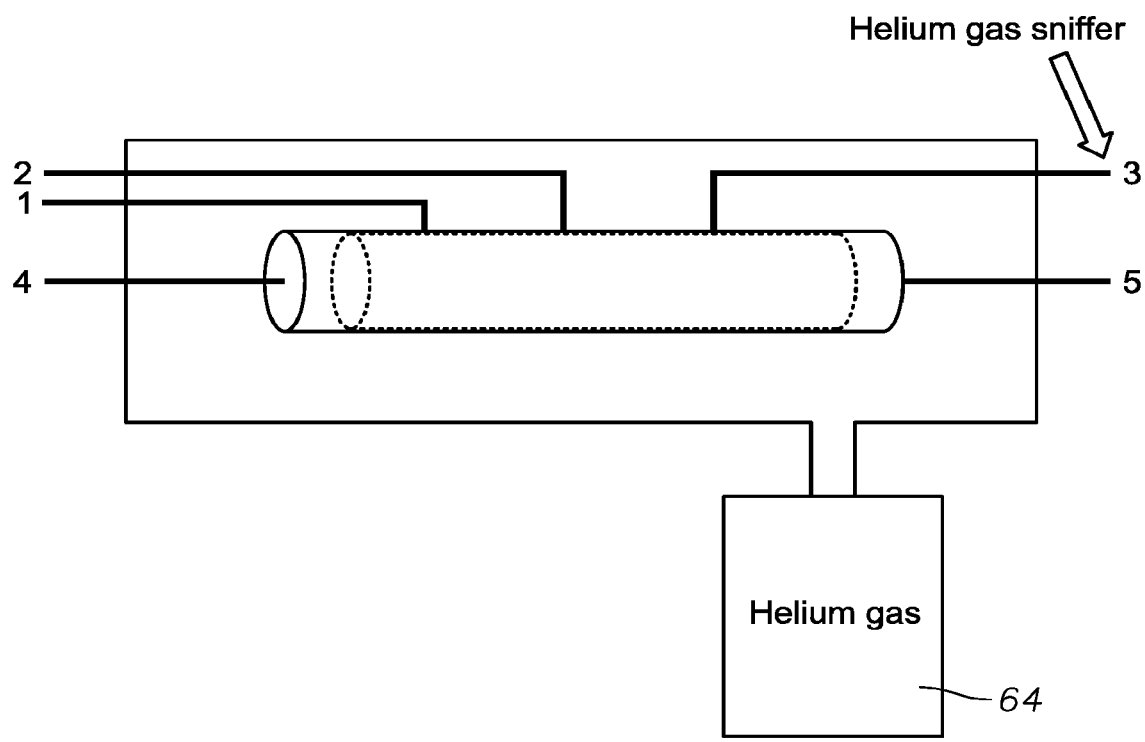

In FIG. 6B, the sample assembly is put into a measurement cell 50 with an intlet 62. It should be noted, however, that the lines 1-5 can come out of the cell 50 from any direction, and the gas lines do not necessarily have to be straight. For example, FIG. 6C illustrates a system 100 where side lines 1, 2, 3 exit the measurement cell 50 on either sides of the measurement cell 50. As an optional step, the opening of the lines can be plugged, except one, such that the sample 30 is vacuumed to remove residual fluid inside the rock sample 30. Next, a helium gas tank 64 is coupled to the measurement cell 50, as shown in FIG. 6D, thereby confining the fluid in the cell 50. Helium gas pressure is then raised up to a predetermined value. Generally, a pressure above 100 psi is recommended. Finally, helium gas leaking into the sample 30 through the side holes 65 can be detected at the open port of each line 1, 2, 3, 4, 5 from which gas can come out. FIG. 6E illustrates one embodiment where the helium gas sniffer is attached to side line 3 and the other lines are plugged. In some cases, the plug needs to be removed if tested open port is plugged. In another embodiment, a commercial helium gas sniffer that can detect minimum gas flow rate at $1 \times 10^{-7}$ cubic centimeter per second (cc/s) can be used to detect leakages of any size.

In one embodiment, helium gas sniffers may be coupled to each of the lines 1, 2, 3, 4, 5 from which the gas can come out. As a result, if gas leakage is detected, the leak position can be determined from the line(s) associated with helium leakage. The sample assembly can then be taken out of the cell and the connections can be reworked. If no gas leakage is detected, the lines can be coupled to the proper transducers or reservoirs, and the permeability measurement can be performed.

Accordingly, one embodiment is a method for detecting leakage in a permeability measurement system. The method includes extracting a core sample 30 from a subsurface formation, inserting the core sample 30 in a cylindrical sleeve 52 to form a sample assembly 300, connecting a plurality of flow lines along the length of the core sample 30, connecting a first flow line to the first end of the core sample 30, connecting a second flow line to the second end of the core sample 30, and connecting a gas sensor to ends of each of the flow lines. In one embodiment, the inner diameter of the sleeve 52 is approximately equal to the diameter of the core sample 30.

The method further includes placing the sample assembly 300 with the connections in a measurement cell 50 such that the flow lines are accessible from outside of the measurement cell 50, connecting an inlet of the measurement cell 50 to a gas tank 64, setting fluid pressure inside the measurement cell 50 to a predetermined value and detecting a leakage in the sample assembly 300 by one or more of the gas sensors connected to one end of each of the flow lines. The core sample 30 may have a cylindrical shape with a length, a diameter, a first end, and a second end.

The method may further include saturating the core sample 30 with a predetermined gas at a predetermined pressure prior to placing the sample assembly 300 inside the measurement cell 50. The gas sensor may include a helium gas sniffer, and may include any type of sensor including but not limited to a combustible gas sensor, a photoionization detector, an infrared point sensor, an infrared imaging sensor, an ultrasonic sensor, an electrochemical gas sensor, a holographic sensor, and a metal-oxide-semiconductor sensor. According to one embodiment, the gas sensor is able to detect a minimum gas flow rate of $1 \times 10^{-7}$ cubic centimeter per second (cc/s), because the measurement of permeability and porosity of the rock formation can be impacted due to even the slightest leakage in the system, and the method disclosed determines a precise location of the leakage based on the flow line(s) detecting the leakage. The gas tank 64 may include at least one of helium, nitrogen, argon, oxygen, and combinations thereof. Although the above example refer to a shale sample, the core sample may include any of shale, sandstone, or limestone.

Figure 7:
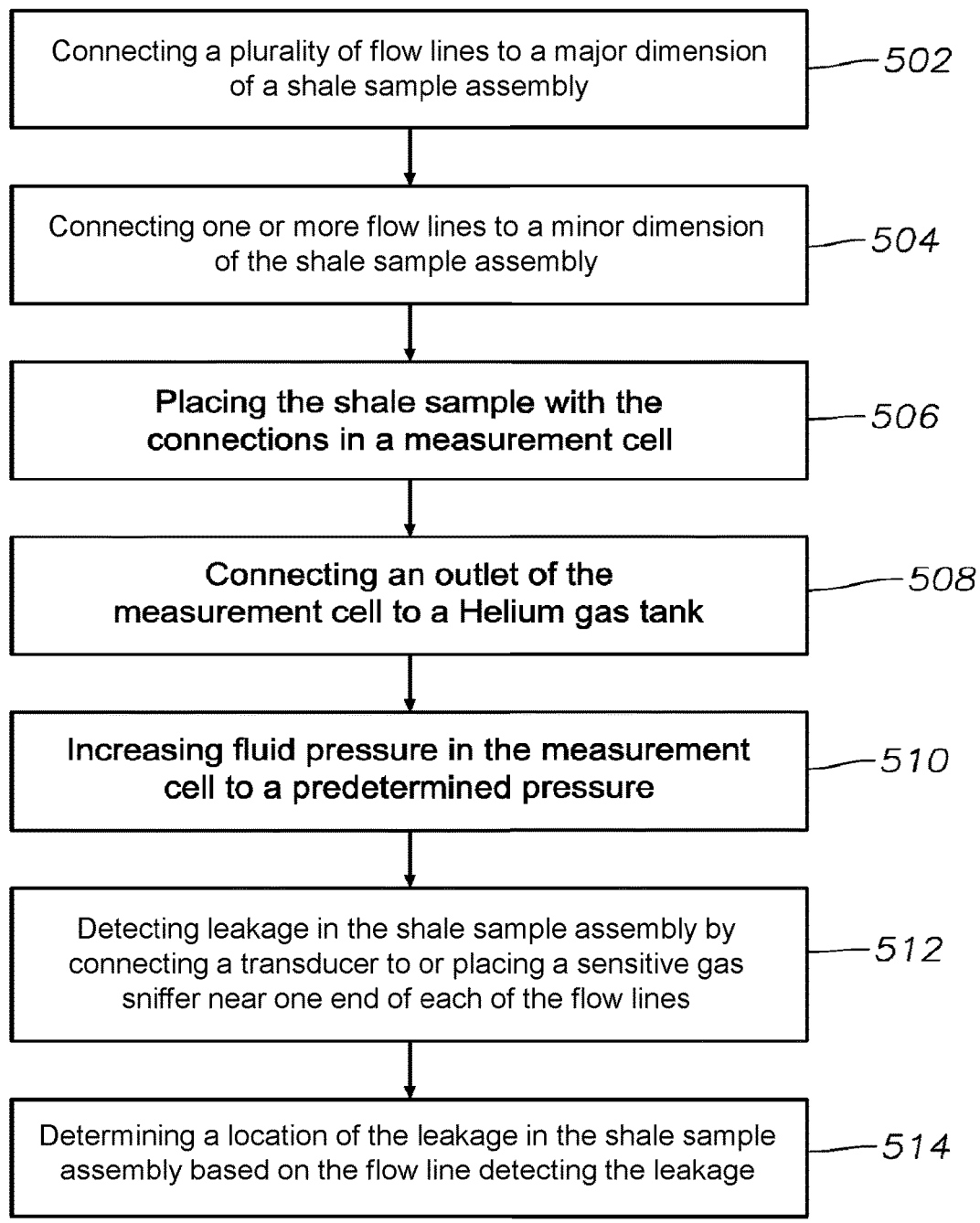
FIG. 7 shows a flow chart illustrating example operations in a method for detecting leakage in a system for determining permeability and porosity of a subsurface rock formation, according to one example embodiment of the disclosure.

Turning now to FIG. 7, illustrated is a flow chart showing example operations in a method 500 for detecting leakage in a permeability measurement system, according to one or more example embodiments. At step 502, a plurality of flow lines are coupled to a first dimension of a shale sample assembly containing a shale sample, such as along the length of the sample, and these coupled to the first dimension may be called sidetap connections. At step 504, one or more flow lines are coupled to a second dimension of the shale sample assembly, such as to the cylindrical surface of the sample, and these coupled to the second dimension may be called inlet or outlet connections. At step 506, the shale sample containing the shale sample with its connections is placed in a measurement cell such that the flow lines are accessible from outside of the measurement cell. One or more transducers, such as a helium gas sniffer, may be coupled to or placed near one end of each of the flow lines. At step 508, one inlet of the measurement cell is coupled to a helium gas tank. At step 510, the fluid pressure inside the measurement cell is increased to a predetermined pressure by letting in the helium gas from the helium gas tank. At step 512, any leakage in the shale sample assembly is detected by the transducer coupled to the flow lines or gas sniffers placed near the end of the flow lines. At step 514, the location of the leakage can be determined based on the flow line(s) detecting the leakage, as the flow lines are directly coupled to the shale sample assembly on one end.

Figure 8:
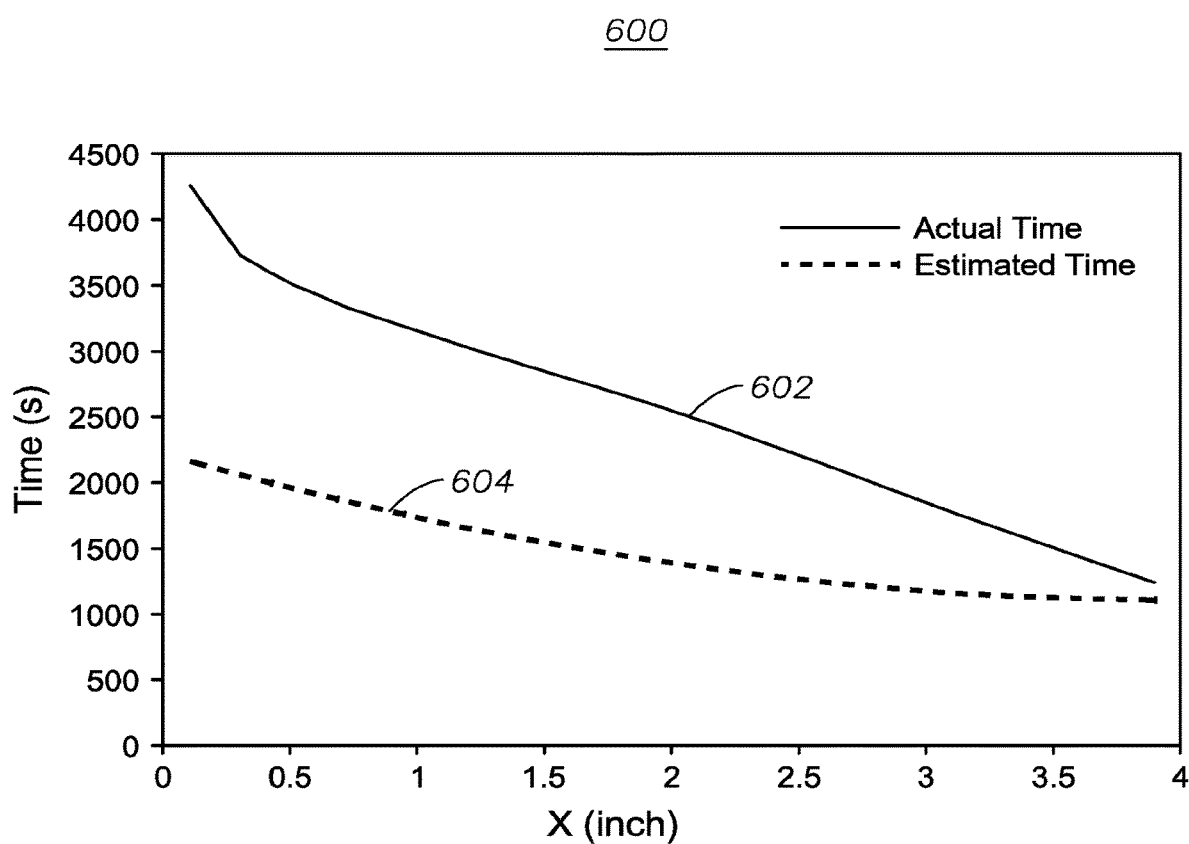
FIG. 8 shows a graphic illustrating simulated time values when the boundary effect occurs (actual time) and estimated time at different locations along a shale formation sample, according to one example embodiment of the disclosure.

The disclosed method is based on an analytical solution that may be suitable for a sample of any size. However, in the experimental data a 4 inches long shale column is used in combination with pressure data before time $t_c$ given in Equation 14. FIG. 8 shows a graphic illustrating simulated time values 600 (based on Equation 1 and related boundary and initial conditions) when the boundary effect occurs (actual time from simulation) 602 and estimated time (from Equation 14) 604 at different locations along a shale formation sample, according to one example embodiment of the disclosure. The initial pore gas pressure in a sample may be 100 psi. Pressure at the inlet may be instantaneously raised to 1000 psi at t>0. Gas density and viscosity in Equation 1 may be treated as functions of pore gas pressure. Two columns with lengths of 4 inches and 12 inches are used in the simulations. No pore gas pressure breakthrough is observed for the long column during the test time periods; therefore it can be treated as an infinitely long column. The simulated pressures at different locations for both columns are compared. The outlet boundary effect is considered to occur at a time when the pressure difference for the two columns at a location is larger than 0.1 psi. As it can be seen, estimates from Equation 14 are smaller than the simulated time values. Thus, Equation 14 can be considered to be on the conservative side. It is reliable to treat pressure data collected for t<$t_c$ as those corresponding to an infinitely long column. As a result, for a 4-inch long shale sample, the no-flow boundary effect can be minimized at X=1 inch. The valid time period for pressure measurement (0-3000 s) can cover a pressure range of approximately 100-750 psi for the given example.

Numerical experiments are also conducted to check if the test procedure gives the "true" pressure-dependency of shale gas permeability. In a numerical experiment, the "true" permeability is that used as model input. Observed pressure data from the location about 1 inch away from the inlet are used and random errors with magnitude of 0.2 psi are added to the simulated pressures to consider the pressure measurement errors. As indicated by the line 602 in FIG. 8, the time when the no-flow boundary affects the pressure response in upstream locations increases with the distance to the no-flow boundary. So in order to ensure enough time for valid measurements, the pressure gauge should be put at a predetermined distance away from the boundary. However at the same time, it should not be close to the inlet because the pressure response there increases from $p_i$ to $p_0$ rapidly. In the present method, the measurement location is at X=1 inch.

While doing the actual measurements, an estimated time for valid measurements can be calculated using Equation 14. The dotted line 604 (calculated from Equation 14) in FIG. 8 indicates that it is a conservative estimation and thus can be safely used in practice.

Figure 9:
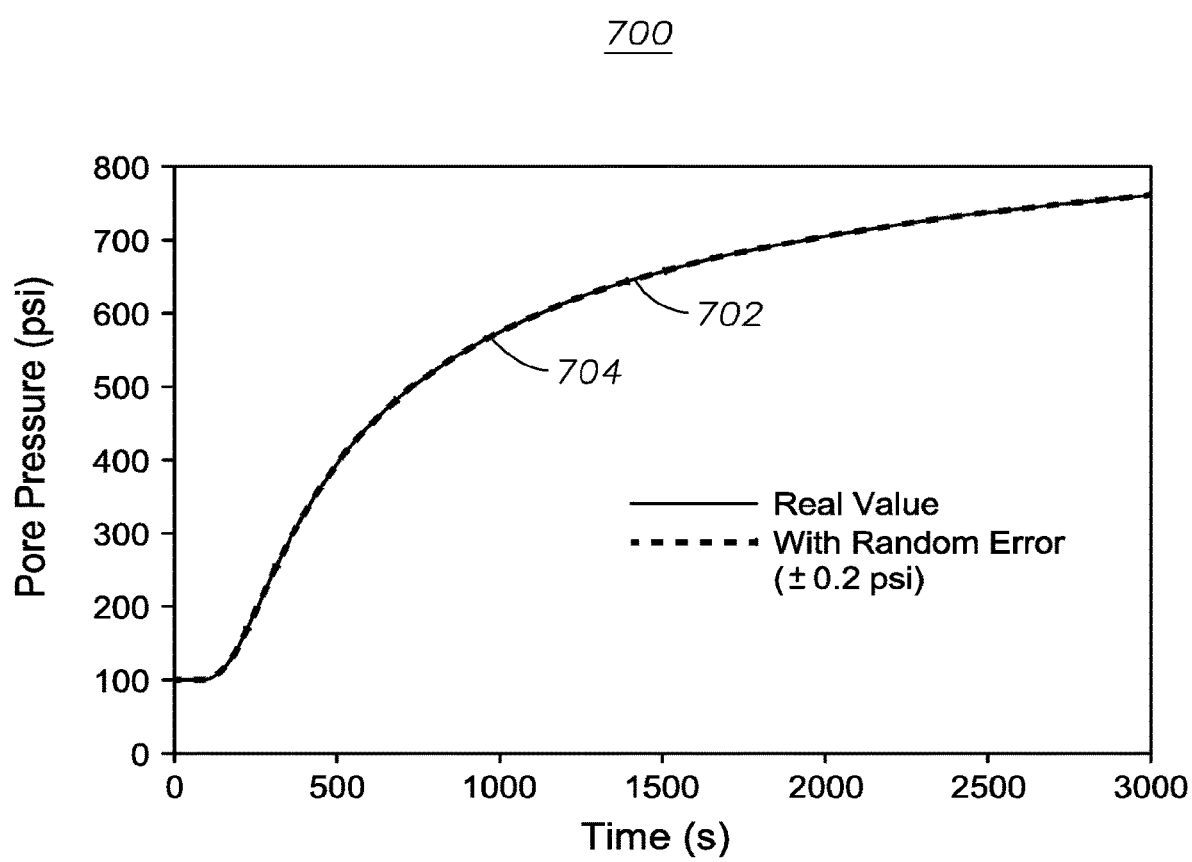
FIG. 9 shows a graphic illustrating simulated gas pore gas pressure, real value and with random error of +/−0.2 pounds per square inch (psi), as a function of time at the core location about one inch away from the inlet, according to one example embodiment of the disclosure.

FIG. 9 shows a graphic illustrating simulated gas pore gas pressure 700, real value 702 and with random error of +/−0.2 psi 704, each as a function of time at the core location about one inch away from the inlet, according to one example embodiment of the disclosure. The addition of random error does not make considerable difference in the pressure distribution because pressure measurement error is generally small, for example around 0.1 psi.

Figure 10:
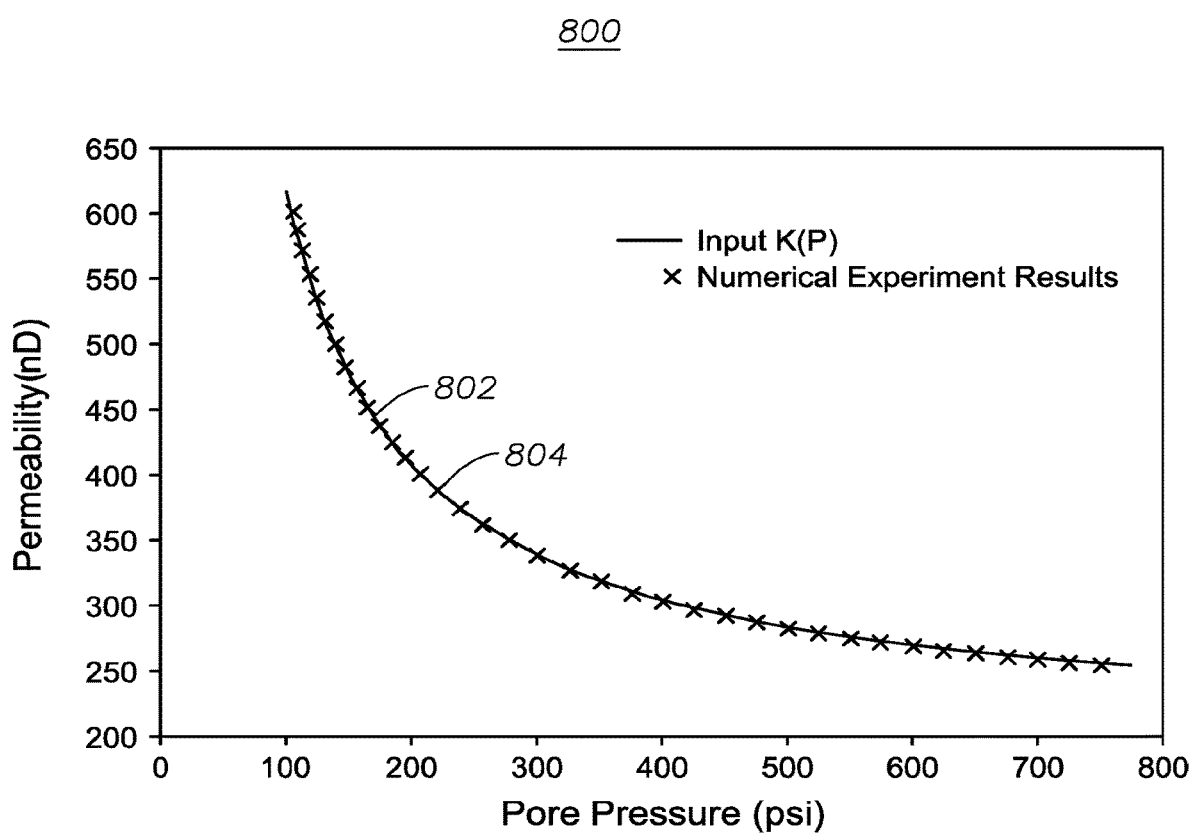
FIG. 10 shows a graphic illustrating comparison between the true permeability as a function of pore gas pressure and the permeability from numerical experiment results, according to one example embodiment of the disclosure.

FIG. 10 shows a graphic illustrating comparison between the measured permeability as a function of pore gas pressure and the permeability from numerical experiment results, according to one example embodiment of the disclosure. As shown in the graph 800 in FIG. 10, results 804 based on the laboratory test procedure discussed in the previous section with input k(p) and pressure data from numerical experiments are almost identical to the measured values 802 (or input k(p)), indicating that the proposed procedure is accurate and reliable. It can be observed that they are highly consistent with each other, which also means that the recorded pressure response is very close to that in the theoretical model and the boundary effect is minimized at location X=1 inch.

Computer Readable Medium

Figure 11:
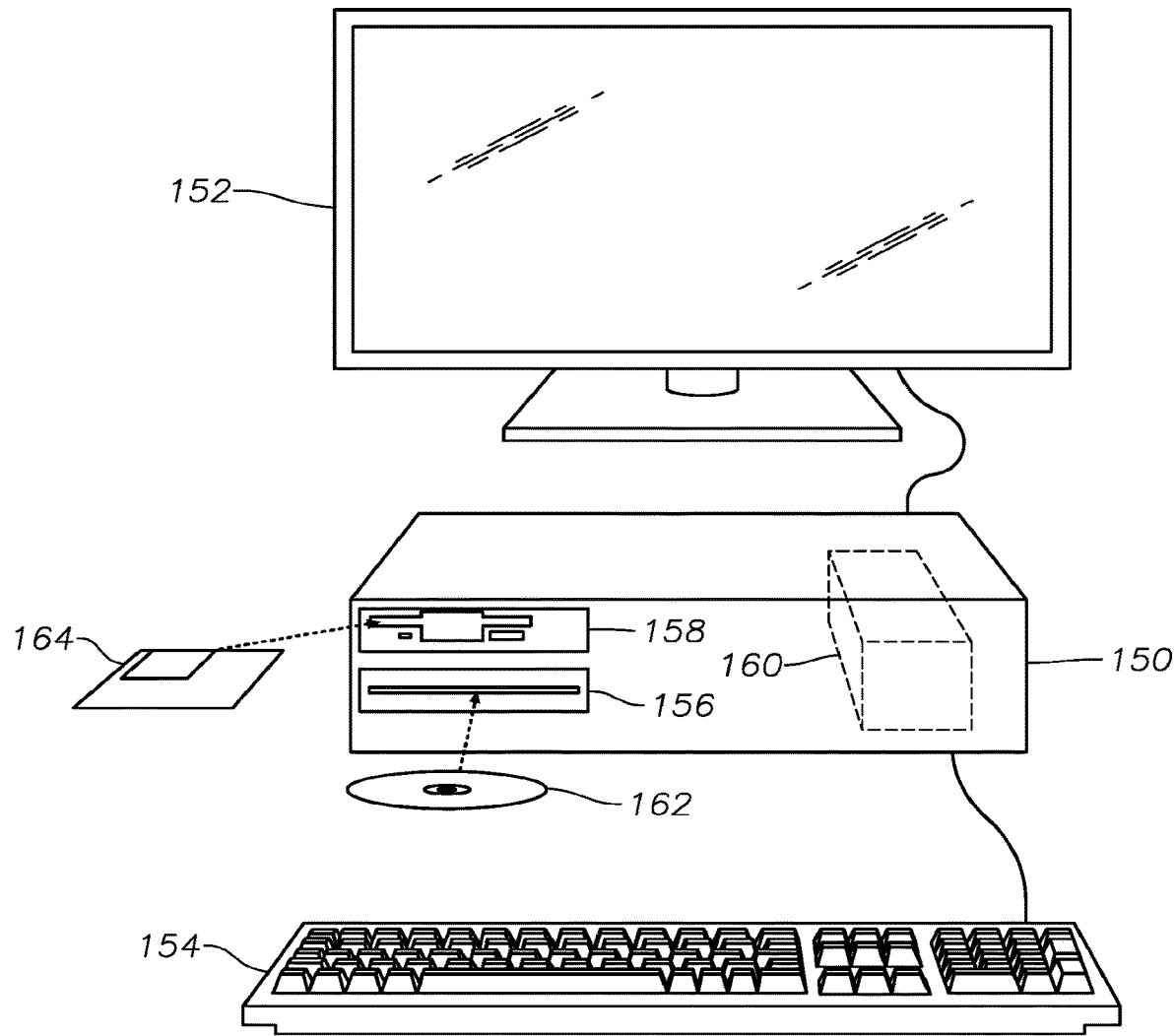
FIG. 11 shows a programmable computer and various forms of computer readable media that form a part of the system for detecting leakage in a system for determining permeability and porosity of a subsurface rock formation, according to some example embodiments of the disclosure.

Another example embodiment is a computer program stored in computer readable media. Referring to FIG. 11, the foregoing process as explained with reference to FIGS. 1-10 can be embodied in computer-readable code for detecting leakage in a permeability measurement system and to measure permeability and/or porosity of the subsurface formation. The code can be stored on, for example, a computer readable medium, such as a floppy disk 164 which may be read by a disk drive 158, CD-ROM 162 which may be read by a disk drive 156, or a magnetic (or other type) hard drive 160 forming part of a general purpose programmable computer. The computer, as known in the art, includes a central processing unit 150, a user input device such as a keyboard 154 and a user display 152 such as a flat panel LCD display or cathode ray tube display. According to one example embodiment, the gas sensors depicted in FIGS. 6A-6E may be connected to processor or central processing unit 150 in the computer system.

According to this aspect, the computer readable medium includes logic operable to cause the computer to execute acts as set forth previously and explained with respect to the previous figures. The non-transitory computer-readable medium having computer executable instructions cause a computer to perform the operations of reading a measurement of a first pore gas pressure, $p_i$, inside a sample assembly 300 comprising a sample of a subsurface formation, gas, and a pressure gauge. The instructions also include reading a measurement of a second pore gas pressure, $p_o$, applied to the inlet of a sample, where the second pore gas pressure is greater than the first pore gas pressure. The instructions also include reading a measurement of a third pore gas pressure, p, at location x at time t in the sample, and determining a total gas mass per unit volume of the subsurface formation, m. The instructions also include determining a permeability of the subsurface formation, k, based at least in part on the first pore gas pressure, the second pore gas pressure, the third pore gas pressure, and the gas density.

The computer executable instructions further cause the computer to perform the operation of determining the transport parameter of the subsurface formation, D(p), using a first formula:

$$D(p) = -\frac{\int_{p_i}^{p} \frac{\lambda}{2} \frac{dm}{dp} dp}{\frac{\partial p}{\partial \lambda}}$$

where $p_i$ is the first pore gas pressure inside the sample in assembly 300 before the second pore gas pressure $p_o$ is applied, p is the third pore gas pressure at location x at time t, m is the total gas mass per unit volume of the subsurface formation, and λ is an independent variable calculated using the formula $xt^{-1/2}$. Then permeability can be determined from D(p) using Equation 9.

The computer executable instructions further cause the computer to perform the operation of determining the total gas mass per unit volume of the subsurface formation, m, using a second formula:

$$m = \phi\rho + (1-\phi)\rho_a$$

where ϕ is porosity of the subsurface formation, ρ is gas density of the natural gas, and $\rho_a$ is adsorbed gas mass per unit volume of the subsurface formation.

The computer executable instructions further cause the computer to perform the operation of determining the porosity $\phi$ of the subsurface formation using a third formula:

$$\phi = \frac{B - A \int_{P_i}^{P_0} \lambda \frac{d\rho_a}{dp} dp}{A \int_{P_i}^{P_0} \lambda \frac{d(\rho - \rho_a)}{dp} dp}$$

where A is a cross-sectional area of the sample, and B is a slope of a curve of the cumulative gas flow into the sample at x=0 versus $t^{1/2}$.

The computer executable instructions further cause the computer to perform the operation of determining the slope of the curve, B, using a fourth formula:

$$B = A \int_{P_i}^{P_0} \lambda \frac{dm}{dp} dp$$

Methods disclosed here may provide improved estimates of permeability as a function of pore gas pressure and porosity of subsurface rock formations. Analytical models used to measure pressure-dependent gas permeability of shale are disclosed. Example methods and systems to measure shale gas permeability as a function of pore gas pressure are disclosed. The advantages of this approach over the currently available ones include that it measures pressure-dependent gas permeability more efficiently using a single test run and without any presumption regarding a parametric relationship between gas permeability and pressure. In addition, the disclosed embodiments also allow for estimating shale porosity from the related measurements.

The Specification, which includes the Summary, Brief Description of the Drawings and the Detailed Description, and the appended Claims refer to particular features (including process or method steps) of the disclosure. Those of skill in the art understand that the invention includes all possible combinations and uses of particular features described in the Specification. Those of skill in the art understand that the disclosure is not limited to or by the description of embodiments given in the Specification.

Those of skill in the art also understand that the terminology used for describing particular embodiments does not limit the scope or breadth of the disclosure. In interpreting the Specification and appended Claims, all terms should be interpreted in the broadest possible manner consistent with the context of each term. All technical and scientific terms used in the Specification and appended Claims have the same meaning as commonly understood by one of ordinary skill in the art to which this invention belongs unless defined otherwise.

As used in the Specification and appended Claims, the singular forms "a," "an," and "the" include plural references unless the context clearly indicates otherwise. The verb "comprises" and its conjugated forms should be interpreted as referring to elements, components or steps in a non-exclusive manner. The referenced elements, components or steps may be present, utilized or combined with other elements, components or steps not expressly referenced. The verb "operatively connecting" and its conjugated forms means to complete any type of required junction, including electrical, mechanical or fluid, to form a connection between two or more previously non-joined objects. If a first component is operatively connected to a second component, the connection can occur either directly or through a common connector. "Optionally" and its various forms means that the subsequently described event or circumstance may or may not occur. The description includes instances where the event or circumstance occurs and instances where it does not occur.

Conditional language, such as, among others, "can," "could," "might," or "may," unless specifically stated otherwise, or otherwise understood within the context as used, is generally intended to convey that certain implementations could include, while other implementations do not include, certain features, elements, and/or operations. Thus, such conditional language generally is not intended to imply that features, elements, and/or operations are in any way required for one or more implementations or that one or more implementations necessarily include logic for deciding, with or without user input or prompting, whether these features, elements, and/or operations are included or are to be performed in any particular implementation.

The systems and methods described herein, therefore, are well adapted to carry out the objects and attain the ends and advantages mentioned, as well as others inherent therein. While example embodiments of the system and method have been given for purposes of disclosure, numerous changes exist in the details of procedures for accomplishing the desired results. These and other similar modifications may readily suggest themselves to those skilled in the art, and are intended to be encompassed within the spirit of the system and method disclosed herein and the scope of the appended claims.

The invention claimed is:

1. A method for detecting leakage in a permeability measurement system comprising a sample assembly, the method comprising:
    extracting a core sample from a subsurface formation, the core sample having a cylindrical shape with a length, a diameter, a first end, and a second end;
    inserting the core sample in a cylindrical sleeve to form the sample assembly;
    connecting a plurality of flow lines through the sample assembly to the core sample along the length of the core sample;
    connecting a first flow line to the first end of the core sample;
    connecting a second flow line to the second end of the core sample;
    connecting a gas sensor to ends of each of the flow lines;
    placing the sample assembly containing the core sample with the connections in a measurement cell such that the flow lines are accessible from outside of the measurement cell;
    connecting an inlet of the measurement cell to a gas tank;
    setting gas pressure inside the measurement cell to a predetermined value; and
    detecting a leakage in the system by one or more of the gas sensors connected to one end of each of the flow lines.

2. The method of claim 1, further comprising: saturating the core sample with a predetermined gas at a predetermined pressure prior to placing the sample assembly inside the measurement cell.

3. The method of claim 1, wherein the gas sensor comprises a helium gas sniffer.

4. The method of claim 1, wherein the gas sensor comprises at least one of a combustible gas sensor, a photoionization detector, an infrared point sensor, an infrared imaging sensor, an ultrasonic sensor, an electrochemical gas sensor, a holographic sensor, and a metal-oxide-semiconductor sensor.

5. The method of claim 1, wherein the gas sensor detects a minimum gas flow rate of $1 \times 10^{-7}$ cubic centimeter per second (cc/s).

6. The method of claim 1, wherein the gas tank comprises at least one of helium, nitrogen, argon, oxygen, and combinations thereof.

7. The method of claim 1, further comprising:
determining a precise location of the leakage based on the flow line(s) detecting the leakage.

8. The method of claim 1, wherein an inner diameter of the sleeve is approximately equal to the diameter of the core sample.

9. The method of claim 1, wherein the core sample comprises shale, sandstone, or limestone.

10. An apparatus for detecting leakage in a permeability measurement system comprising a sample assembly, comprising:
a cylindrical sleeve and a core sample of a subsurface formation disposed within the sleeve, the core sample having a cylindrical shape with a length, a diameter, a first end, and a second end;
a plurality of flow lines connected along the length of the core sample;
a first flow line connected to the first end of the core sample;
a second flow line connected to the second end of the core sample;
gas sensor connected to ends of each of the flow lines;
a measurement cell configured to receive the sample assembly containing the core sample such that the flow lines are accessible from outside of the measurement cell; and
a gas tank connected to an inlet of the measurement cell, wherein a gas pressure inside the measurement cell is set to a predetermined value, wherein the gas sensors are configured to detect a leakage in the system.

11. The apparatus of claim 10, wherein the core sample is saturated with a predetermined gas at a predetermined pressure prior to placing the sample assembly inside the measurement cell.

12. The apparatus of claim 10, wherein the gas sensor comprises a helium gas sniffer.

13. The apparatus of claim 10, wherein the gas sensor comprises at least one of a combustible gas sensor, a photoionization detector, an infrared point sensor, an infrared imaging sensor, an ultrasonic sensor, an electrochemical gas sensor, a holographic sensor, and a metal-oxide-semiconductor sensor.

14. The apparatus of claim 10, wherein the gas sensor detects a minimum gas flow rate of $1 \times 10^{-7}$ cubic centimeter per second (cc/s).

15. The apparatus of claim 10, wherein the gas tank comprises at least one of helium, nitrogen, argon, oxygen, and combinations thereof.

16. The apparatus of claim 10, wherein the apparatus is configured to determine a precise location of the leakage based on the flow line(s) detecting the leakage.

17. The apparatus of claim 10, wherein an inner diameter of the sleeve is approximately equal to the diameter of the core sample.

18. The apparatus of claim 10, wherein the sleeve has a length, a diameter, a first open end, and a second open end;
a first end piece adapted to be inserted into the first open end and a second end piece adapted to be inserted into the second open end of the sleeve;
a first hole formed through the first end piece and into a body of the core sample of the subsurface formation housed in the sleeve; and
a second hole formed through the second end piece and into the body of the core sample of the subsurface formation housed in the sleeve.

19. The apparatus of claim 10, wherein the sleeve comprises at least two ports connecting the core sample assembly to at least one pump, at least one port for applying a confining pressure, and at least one port for measuring pressure located at a known location along the core sample.

20. The apparatus of claim 10, wherein the core sample comprises shale, sandstone, or limestone.

* * * * *